United States Patent [19]

Cox et al.

[11] 4,434,091

[45] Feb. 28, 1984

[54] NOVEL SULPHOSUCCINATES AND DETERGENT COMPOSITIONS CONTAINING THEM

[75] Inventors: Ian R. Cox; Keith Jones, both of Wirral, England

[73] Assignee: Lever Brothers Company, New York, N.Y.

[21] Appl. No.: 400,794

[22] Filed: Jul. 22, 1982

[30] Foreign Applications Priority Data

Jul. 24, 1981 [GB] United Kingdom ............ 8122831

[51] Int. Cl.$^3$ ...................... C11D 1/16; C07C 149/20
[52] U.S. Cl. ..................................... 252/557; 252/545; 252/551; 252/553; 252/558; 252/DIG. 14; 560/151
[58] Field of Search ............... 252/538, 557, DIG. 14; 560/151

[56] References Cited

U.S. PATENT DOCUMENTS

| | | | |
|---|---|---|---|
| 2,028,091 | 1/1936 | Jaeger | 560/151 |
| 2,181,087 | 11/1939 | Caryl et al. | 252/557 |
| 2,917,431 | 12/1959 | Di Cicco | 252/525 X |

FOREIGN PATENT DOCUMENTS 1429637  3/1976  United Kingdom .

*Primary Examiner*—P. E. Willis, Jr.
*Attorney, Agent, or Firm*—Milton L. Honig; James J. Farrell

[57] ABSTRACT

The invention provides novel dialkyl sulphosuccinates in which one alkyl group is $C_6$ and the other is $C_8$, both alkyl groups preferably being straight chain. The soluble salts of these materials are useful detergents, exhibiting outstandingly good foaming performance, and may be used, for example, in shampoos, fabric washing compositions and, in particular, manual dishwashing compositions.

5 Claims, No Drawings

NOVEL SULPHOSUCCINATES AND DETERGENT COMPOSITIONS CONTAINING THEM

The present invention relates to certain novel detergent-active sulphosuccinate materials, and to their use in detergent compositions suitable for many purposes, for example, fabric washing products, general purpose domestic and industrial cleaning compositions, carpet shampoos, car wash products, personal washing products, shampoos, foam bath products, and above all, compositions for use in dishwashing operations in both hard and soft water.

The term "dishes" as used herein means any untensils involved in food preparation or consumption which may be required to be washed to free them from food particles and other food residues, greases, proteins, starches, gums, dyes, oils and burnt organic residues.

Light-duty liquid detergent compositions such as are suitable for use in washing dishes are well known. Most of the formulations in commercial use at the present time are based on anionic synthetic detergents with or without a nonionic detergent. Many of such formulations contain a sulphonate-type anionic detergents, for example, an alkylbenzene sulphonate or an alkane sulphonate, in conjunction with a sulphate-type anionic detergent, for example, an alkyl sulphate or an alkyl ether sulphate, or a nonionic detergent, for example, an alcohol ethoxylate, an alkyl phenol ethoxylate, a mono- or diethanolamide, or an amine oxide. The sulphonate material generally predominates.

Alkylbenzene sulphonates and alkane sulphonates are produced by sulphonation of petrochemically derived hydrocarbons and consist of a mixture of materials of different chain lengths and sulphonate group substitution only some of which contribute to the cleaning and foaming performance of the product, different materials being useful at different water hardnesses. The chemistry of manufacture of these materials allows at best limited control of the isomer distribution in the product alkylbenzene sulphonates and secondary alkane sulphonates.

Dialkyl sulphosuccinates and their use as surface-active agents are disclosed in U.S. Pat. No. 2,028,091 (American Cyanamid). This document refers inter alia to dialkyl sulphosuccinates in which the two alkyl groups are derived from two different alcohols, for example, the mixed amyloctyl sulphosuccinates.

GB. No. 1,429,637 (Unilever) discloses hand dishwashing compositions containing as detergent-active material a water-soluble salt of a di($C_7$-$C_9$)alkyl ester of sulphosuccinic acid, in combination with an alkyl sulphate or an alkyl ether sulphate. These compositions show good foaming and cleaning properties which are sharply dependent on the chain length of the dialkyl sulphosuccinates, the di(n-$C_6$) and di(n-$C_{10}$) compounds giving very poor results compared with the di($C_7$-$C_9$) compounds.

It has now surprisingly been found that a class of unsymmetrical dialkyl sulphosuccinates not specifically described in the literature show a substantially better foaming and cleaning performance that would be expected from the performance of similar, related compounds.

These materials may be used, alone or together with other sulphosuccinates or other detergent-active materials, to form the basis of highly efficient detergent compositions, especially liquid detergent compositions, which are suitable inter alia for hand dishwashing.

The present invention accordingly provides a compound of the formula I:

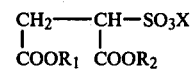

wherein one of $R_1$ and $R_2$ represents a $C_6$ alkyl group and the other represents a $C_8$ alkyl group, and X represents a monovalent cation or 1/m of an m-valent cation.

Compounds wherein X represents a solubilising cation are detergent-active and such compounds are especially preferred. By "solubilising cation" is meant any cation yielding a salt of the formula I sufficiently soluble to be detergent active. Such cations will generally be monovalent, for example, alkali metal, especially sodium; ammonium; substituted ammonium, for example, ethanolamine. Certain divalent cations, notably magnesium, are also solubilising in this sense.

The groups $R_1$ and $R_2$ may be straight-chain or branched-chain; compounds in which at least one of the R groups is a straight-chain alkyl group are preferred and compounds in which both R groups are straight-chain are especially preferred.

The compounds of the invention may be synthesised by various methods. The synthesis of symmetrical dialkyl sulphosuccinates is well documented in the literature; see, for example, the above-mentioned U.S. Pat. No. 2,028,091 (American Cyanamid).

According to a preferred method, maleic anhydride (or maleic acid or fumaric acid, but preferably maleic anhydride) is esterified with an appropriate alkanol, in the presence of an acid catalyst such as p-toluene sulphonic acid, to give the corresponding dialkyl maleate/fumarate (I) which is then subjected to bisulphite addition to give the dialkyl sulphosuccinate (II):

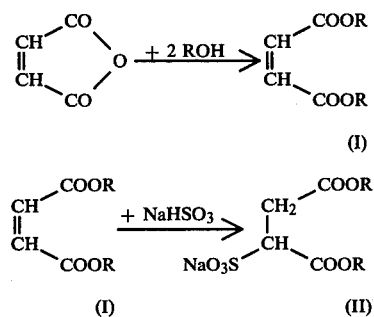

Esterification of maleic anhydride (or maleic acid or fumaric acid) with a single alcohol gives a single product in which both alkyl groups are the same. If, however, a mixture of two alcohols is used, a mixture of symmetrical and unsymmetrical products is obtained. Hence the compounds of the invention may be produced, in conjunction with the di$C_8$ and di$C_6$ symmetrical compounds, by esterifying maleic anhydride or its equivalents with a mixture of $C_6$ and $C_8$ alkanols, followed by sulphitation of the resultant esters. If an equimolar mixture of the starting alcohols is used, one would expect statistically about 50 mole percent of unsymmetrical material according to the invention (isomer mixture, because the two alkyl groups in the sulphosuccinate are not in equivalent positions) and about 25 mole percent each of the two symmetrical materials.

This synthetic route is not suitable for the preparation of the pure unsymmetrical material because of the difficulty in separating the symmetrical and unsymmetrical diesters (I): because of the similarity of chain-length the boiling points of the three materials are too close for fractional distillation to be conveniently possible.

The final sulphosuccinate mixture is, however, itself a highly efficient detergent-active agent, and it will not normally be necessary to make any attempt to separate the constituents. Mixtures of this type are described and claimed in our co-pending Application of even date entitled "Detergent Compositions" (Case C.1304).

To prepare the individual unsymmetrical material of the invention it is necessary to avoid the formation of a statistical mixture of maleate/fumarate diesters by first preparing a monoester, by esterification by one alcohol under controlled conditions, and then subjecting the monoester to selective esterification by the second alcohol or a derivative thereof to give the unsymmetrical diester. This reaction scheme may be represented schematically as follows:

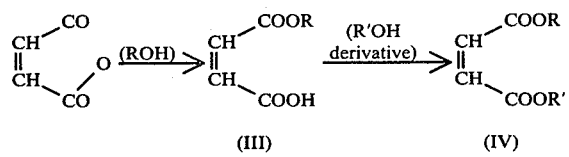

(III)                    (IV)

The first step, preparation of a pure monoester (III), may be achieved by heating the alcohol with maleic anhydride in a solvent such as toluene in the absence of an acid catalyst. A mixture of monoester and symmetrical diester is obtained, together with a significant amount of unreacted alcohol, and these can be separated without difficulty, for example, by recrystallisation from petroleum ether.

The second step must be carried out under non-equilibrium conditions in order to avoid reversibility of the reaction, which would generate a statistical mixture of symmetrical and unsymmetrical diesters. Two methods have been developed, both of which involve reaction of an alkali metal salt of the monoester (III) with an alkyl halide, preferably the bromide R'Br, to give the unsymmetrical diester (IV) in yields exceeding 92% isomeric purity.

According to the first method, an aqueous solution of an alkali metal (preferably potassium) salt of the monoester (III) is reacted with a chloroform solution of the alkyl bromide in the presence of a phase transfer catalyst, for example, tetra-n-butyl ammonium bromide or iodide. The unsymmetrical diester (IV) is formed in the chloroform layer, and can be recovered directly by separation, drying and removal of the residual alkyl bromide by distillation. Using tetra-n-butyl ammonium bromide as catalyst, yields of about 45% have been obtained in about 7 hours and, using the iodide catalyst, this figure can be increased to about 65%. It is believed that the reaction takes place as follows: the carboxylate (III) is transferred from the aqueous phase, as an ion pair with the tetra-n-butyl ammonium ion, to the organic phase where it displaces the bromine of the alkyl bromide to form the diester (IV).

According to the second method, the alkyl bromide R'Br is reacted with the alkali metal salt of the monoester (III) in a dipolar aprotic solvent, for example, dimethyl formamide, dimethyl sulphoxide, or hexamethyl phosphoric triamide. The high dielectric constant of the solvent enables all reagents to be in the same phase, but the carboxylate anion of the monoester III is only weakly solvated, thus enhancing its reactivity. No catalyst is needed. The lithium salt of the monoester (III) is preferably used, for maximum solubility, and a relatively high temperature (for example 90° C.) and a relatively prolonged reaction period (for example, about 5 hours) are necessary. The reaction mixture may then be quenched in water and the diester (IV) extracted with ether and purified, for example, by fractional distillation.

When preparing the unsymmetrical $C_6/C_8$ diester of the invention, it has been found convenient to prepare the octyl monoester in the first step and to react it with hexyl bromide. It is, however, equally possible to prepare the hexyl monoester and to react it with octyl bromide.

Finally the unsymmetrical diester may be converted to the corresponding sulphosuccinate by sulphite addition, as previously described for the statistical mixture.

The sulphosuccinates of the invention may be used as the basis of highly efficient detergent compositions. They are advantageously used in conjunction with other sulphosuccinate materials, especially with symmetrical $diC_8$ sulphosuccinates and/or with symmetrical $diC_6$ sulphosuccinates. Mixtures as described and claimed in our co-pending Applications of even date (Cases C.1304 and C.1304/1) are especially preferred.

Detergent compositions according to the invention may if desired contain other detergent-active agents as well as the sulphosuccinate of the invention. These are preferably anionic or nonionic, but may also be cationic, amphoteric or zwitterionic. The type of detergent-active material present in addition to the sulphosuccinate mixture of the invention will depend on the intended end-use of the product. The weight ratio of total sulphosuccinate to other detergent-active material may range, for example, from 99:1 to 1:99.

The invention is, as previously mentioned, especially concerned with manual dishwashing compositions, and in these the sulphosuccinate mixture of the invention may if desired be used in conjunction with other anionic detergents, for example, alkylbenzene sulphonates, secondary alkane sulphonates, α-olefin sulphonates, alkyl glyceryl ether sulphonates, primary and secondary alkyl sulphates, alkyl ether sulphates, and fatty acid ester sulphonates; or with nonionic detergents such as ethoxylated and propoxylated alcohols and ethoxylated and propoxylated alkyl phenols. These materials are well known to those skilled in the art. Materials such as amine oxides and mono- and dialkanolamides, which may be regarded either as nonionic surfactants or as foam boosters, may also be present additionally or alternatively. These materials too are well known to those skilled in the art.

Some of the combinations of detergent-active materials referred to in the two preceding paragraphs will of course be suitable for products other than hand dishwashing compositions.

In formulations intended for hand dishwashing combinations of sulphosuccinates according to the invention with certain other detergent-active materials, notably alkyl ether sulphate and nonionic detergents, are especially preferred. The weight ratio of total sulphosuccinate to these other materials is preferably within the range of from 1:4 to 20:1, more preferably from 1:1 to 12:1. Preferred alkyl ether sulphates are primary and secondary alcohol ethoxy sulphates represented by the general formula $R_1$—O—$(C_2H_4O)_n$—$SO_3M$, in which $R_1$ represents an alkyl group having 10 to 18, carbon atoms, the degree of ethoxylation n is from 1 to 12, and M represents an alkali metal, an ammonium or an amine cation. The $R_1$ group more preferably contains 10 to 15 carbon atoms, and n is more preferably from 1 to 8. In any commercially available ether sulphate, there will of course be a spread of degree of ethoxylation, and n will represent an average value. An example of a suitable amine cation M is the monoethanolamine cation.

Preferred nonionic detergents are in particular the condensates of straight or branched chain primary or secondary aliphatic alcohols with ethylene oxide, of the general formula $R_2$—O—$(C_2H_4O)_m$H, in which $R_2$ is an alkyl group having from 8 to 20 carbon atoms, preferably from 8 to 12 carbon atoms, and m, the average degree of ethoxylation, ranges from 5 to 20.

Other suitable nonionic detergents include nonionic alkylphenol polyethers of the general formula $R_3$—$C_6H_4$—O—$(C_2H_4O)_x$H, where $R_3$ is an alkyl group having from 6 to 16 carbon atoms, preferably 8 to 12 carbon atoms, and the average degree of ethoxylation x is from 8 to 16, preferably 9 to 12; and nonionic condensates of fatty acids and ethylene oxide of the general formula $R_4$—CO—O—$(C_2H_4O)_y$H, where $R_4$ is an alkyl group having from 12 to 18 carbon atoms, and the average degree of ethoxylation y is from 8 to 16.

As previously mentioned, the detergent compositions of the invention are preferably liquids, although the dialkyl sulphosuccinates of the formula I, are themselves solids at ambient temperature. The detergent compositions of the invention may, however, be in any suitable physical form, for example, powders, solid bars or gels. They may be used for any type of detergent product, for example, fabric washing products, general purpose domestic and industrial cleaning compositions, carpet shampoos, car wash products, personal washing products, shampoos, foam bath products, and mechanical and manual dishwashing compositions.

The sulphosuccinate materials with which the invention is concerned are however outstandingly suitable for incorporation in liquid products, with or without other sulphosuccinates or other detergent-active materials. These liquid detergent products may be used for all normal detergent purposes, but are of especial interest for use as fabric washing liquids, both built and unbuilt, for both heavy-duty laundry and for washing delicate fabrics; as shampoos; and, above all, as products for dishwashing, especially for hand dishwashing. These liquid products may range from concentrates, containing virtually 100% active detergent, to the more dilute aqueous solutions seen by the consumer. In the latter type of product the total amount of detergent-active material will generally range from 2 to 60% by weight, the balance being made up by water; minor ingredients such as perfume, colour, preservatives, germicides and the like; and, if necessary, a viscosity and solubility control system, referred to in the art as a hydrotrope. The hydrotrope system may, for example, comprise any one or more of the following materials: lower alcohols, especially ethanol; urea; and lower mono- or dialkylbenzene sulphonates, such as sodium or ammonium xylene sulphonates or toluene sulphonates.

The invention is further illustrated by the following non-limiting Examples.

EXAMPLE 1

(i) Preparation of statistical mixture of $C_6/C_8$ maleates/fumarates

Maleic anhydride (98 g, 1 mole) in toluene (400 ml) contaning octan-1-ol (130 g, 1.0 mole) and hexan-1-ol (102 g, 1.0 mole) and p-toluene sulphonic acid (2 g) was stirred under reflux for 3 hours. Water was removed azeotropically by means of a Dean & Stark apparatus (approximately 18 ml, i.e. 1 mole, of water were collected). The crude reaction mixture was cooled and washed with 30% sodium hydroxide solution, then water, then brine, before drying over anhydrous magnesium sulphate. The mixture was filtered and the solvents removed in vacuo to yield an oil (293 g). This oil was shown by gas-liquid chromatography coupled with mass spectrometry to consist of the symmetrical $diC_8$ diester, the unsymmetrical $C_6/C_8$ diester and the symmetrical $diC_6$ diester in molar proportions of approximately 1:2:1.

(ii) Preparation of Statistical Mixture of $C_6/C_8$ Sulphosuccinates

The oil prepared in Example 1(i), without further purification, was dissolved in industrial methylated spirit (500 ml) and refluxed with 475 ml of a 40% aqueous solution of sodium metabisulphite for 6 hours. The solvent was removed in vacuo to yield a crude solid which was taken up in hot ethanol, filtered hot, and allowed to crystallise at 0° C. A yield of 300 g was obtained, consisting of about 98% detergent-active material and about 0.10–0.15% non-detergent organic matter. By high-performance liquid chromatography it was shown to consist of the $diC_8$, $C_6/C_8$ and $diC_6$ dialkyl sulphosuccinates in molar proportions of approximately 1:2:1.

EXAMPLE 2

Preparation of the Pure $C_6/C_8$ Sulphosuccinates (i) Preparation of Monooctyl Maleate/Fumarate A mixture of octan-1-ol (250 ml, 1.59 mole) and toluene (200 ml) was placed in a 1-liter round bottomed flask fitted with stirrer and condenser. Maleic anhydride (153 g, 1.56 mole) was added and the mixture was stirred under reflux for 2 hours. The toluene was evaporated in vacuo and the resulting oil diluted with 30/40 petroleum ether (1.5 liters). The mixture was filtered and left to crystallise at 4° C. Two crops of crystals were obtained, the total yield being 311 g (87%). The crystals had a melting point of 37° C. and infra-red peaks at 1725 $cm^{-1}$ (C=O) and 1640 $cm^{-1}$ (C=C).

(ii) Preparation of Hexyl/Octyl Maleate/Fumarate

Monooctyl maleic/fumaric acid (88 g, 0.39 mole) was dissolved in chloroform (200 ml) and was stirred in a 1 L Erlenmeyer (Quick Fit) flask, fitted with condenser, with a solution of potassium hydroxide (21 g, 0.38 mole) and tetrabutyl ammonium iodide (15 g, 0.04 mole) in 200 mls of water. To the stirred mixture was added hexyl bromide 64 g, 0.39 mole) and the two phase mixture was stirred rapidly under reflux for 5 hours.

The chloroform layer was separated off, washed with sodium carbonate solution, then with water, and then dried over sodium sulphate. After filtering and evaporating the resulting oil was treated with 30/40 petroleum ether which precipitated the catalyst which could be reused. Filtration/evaporation yielded the crude product as an oil (77 g).

Distillation in vacuo removed 13.1 g hexyl bromide. The yield of undistilled material was 59.3 g (62% based on hexyl bromide). This material was shown, by means of a gas-liquid chromatograph with a flame ionisation detector, to have the following composition (by area): 0.7% $diC_6$ diester, 5% $diC_8$ diester, 93% unsymmetrical diester (76% maleate, 17% fumarate). It had infra-red peaks at 1640 $cm^{-1}$ (C=C) and 1725 $cm^{-1}$ (C=O) and was also identified by $^1H$ NMR and mass spectrometry.

(iii) Preparation of Hexyl/Octyl Sulphosuccinate

Hexyl/octyl maleate/fumarate (50 g, 0.16 mole) was dissolved in methylated spirit (100 ml) and the pH of the mixture was adjusted to about 7.5 with sodium carbonate. The mixture was stirred under reflux for 5 hours with a solution of sodium metabisulphite (60 g) in water (160 ml) in a 3-necked round bottom flask fitted with stirrer and condenser. The hot solution was filtered and set to crystallise. The crude crystals were filtered off, dried and extracted with boiling ethanol. The residual inorganics were filtered off. Evaporation of the filtrate yielded the product as a glassy solid (20 g) which failed to recrystallise from acetone or ethanol. This material contained 92% detergent-active material and 1.5% non-detergent organic matter. It had infra-red peaks at 1735 $cm^{-1}$ (C=O) and 1210-1240 $cm^{-1}$ ($SO_3Na$) and was also identified by $^1H$ NMR.

EXAMPLE 3

Preparation of Pure $C_6/C_8$ Sulphosuccinate
(Alternative Method)

100 g (0.44 mole) of the product of Example 2(i) were dissolved in ethanol (200 ml) and treated with a solution of lithium hydroxide hydrate (20 g, 0.43 mole) in water (100 ml). The solvents were removed in vacuo and the resulting lithium salt was stirred at 90° C. with a solution of hexyl bromide (74 g, 0.44 mole) in dimethyl formamide (200 ml) for 5 hours. The solvent was removed in vacuo and the resulting oil was partitioned between water and ether; the dimethyl formamide washed out of the ether layer.

Analysis of the resulting oil (150 g) by means of a gas-liquid chromatograph with a flame ionisation detector indicated that the composition by area was as follows:

| % | Identity |
|---|---|
| 10 | monooctyl maleic/fumaric acid |
| 2 | dihexyl ester |
| 64.4 | $C_6/C_8$ unsymmetrical maleic ester |
| 17.6 | $C_6/C_8$ unsymmetrical fumaric ester |
| 2 | dioctyl ester |

The unwanted starting acid was removed by extracting an ether solution of the product with sodium carbonate solution. The purified material had infra-red peaks at 1640 $cm^{-1}$ (C=C) and 1725 $cm^{-1}$ (C=O) and was also identified by $^1H$ NMR and mass spectrometry.

The product was converted to the corresponding sulphosuccinate as described in Example 2(iii).

EXAMPLES 4-13

The foaming performances of the sulphosuccinates according to the invention were measured by means of a modified Schlachter-Dierkes test based on the principle described in *Fette und Seifen* 1951, 53, 207. A 100 ml aqueous solution of each material tested, having a concentration of 0.05% active detergent, generally in 5°H or 24°H water (French hardness i.e. 5 or 24 parts calcium carbonate per 100,000 parts water), at 45° C. was rapidly oscillated using a vertically oscillating perforated disc within a graduated cylinder. After the initial generation of foam, increments (0.2 g) of soil (9.5 parts commercial cooking fat, 0.25 parts oleic acid, 0.25 parts stearic acid and 10 parts wheat starch in 120 parts water; in some cases, with 7 parts casein replacing 7 parts of water) were added at 15-second intervals (10 seconds' mild agitation and 5 seconds' rest) until the foam collapsed. The result was recorded as the number of soil increments (NSI score): a score difference of 6 or less is generally regarded as insignificant. Each result was typically the average of 3 or 4 runs.

The di-n-hexyl and di-n-octyl sulphosuccinates used in Examples 4 to 7 and 10 were prepared from n-hexanol and n-octanol respectively by a method analogous to that of Example 1.

EXAMPLE 4

The foaming performance of a sulphosuccinate according to the invention was compared with that of a conventional commercially available dishwashing detergent-active material, namely a $C_{10}$-$C_{12}$ linear alkylbenzene sulphonate (Dobs (Trade Mark) 102 ex Shell), both alone and in the presence of alkyl ether sulphate at a weight ratio of 4:1. The alkyl ether sulphate was a $C_{12}$-$C_{15}$ primary alcohol 3EO sulphate (Dobanol (Trade Mark) 25-3A ex Shell). The sulphosuccinate used was the $C_6/C_8$ compound prepared in Example 2: in the tests where ether sulphate was used, the weight ratio of sulphosuccinate to ether sulphate was 4:1. The results are shown in Table 1.

TABLE 1

|  | 5° H. | | 24° H. | |
|---|---|---|---|---|
|  | Normal soil | Casein soil | Normal soil | Casein soil |
| Alkylbenzene sulphonate | 33 | 9 | 23 | 20 |
| Sulphosuccinate | 53 | 21 | 55 | 68 |
| Alkylbenzene sulphonate/ alkyl ether sulphate | 52 | 9 | 60 | 34 |
| Sulphosuccinate/ alkyl ether sulphate | 53 | 14 | 87 | 48 |

The sulphosuccinate alone is superior to the alkylbenzene sulphonate alone under all four sets of conditions, and is also better than alkylbenzene sulphonate/alkyl ether sulphate in both hard and soft water with casein soil. The addition of alkyl ether sulphate to the sulphosuccinate mix improves its performance still further, except in soft water with casein soil.

EXAMPLE 5

The performance of a pure unsymmetrical $C_6/C_8$ sulphosuccinate prepared as in Example 2 was compared with the performances of the two corresponding symmetrical materials, and the results are shown in Table 2.

TABLE 2

|  | 5° H. | | 24° H. | |
|---|---|---|---|---|
| Material | Normal soil | Casein soil | Normal soil | Casein soil |
| $diC_6$ | 0 | 0 | 0 | 0 |
| $diC_8$ | 40 | 28 | 1 | 37 |

TABLE 2-continued

| | 5° H. | | 24° H. | |
|---|---|---|---|---|
| Material | Normal soil | Casein soil | Normal soil | Casein soil |
| $C_6/C_8$ Measured | 46 | 22 | 52 | 57 |
| (Predicted) | (20) | (14) | (~1) | (18) |

The performance of the $diC_6$ compound was too low to be measured by the test. The predicted score for the $C_6/C_8$ compound was calculated by averaging the scores for the $diC_6$ and $diC_8$ compound; it is accordingly half that of the $diC_8$ compound. The measured score, however, is about the same as that of the $diC_8$ compound in soft water, and substantially better in hard water.

EXAMPLE 6

Example 5 was repeated using a wider range of water hardnesses. The results are shown in Table 3.

TABLE 3

| | 5° H. | | 16° H. | | 24° H. | | 36° H. | |
|---|---|---|---|---|---|---|---|---|
| Material | Normal Soil | Casein Soil | Normal Soil | Casein Soil | Normal Soil | Casein Soil | Normal Soil | Casein Soil |
| $diC_6$ | 0 | 0 | 0 | 0 | 0 | 0 | 0 | 0 |
| $diC_8$ | 35 | 26 | 2 | 36 | 3 | 51 | 3 | 24 |
| $C_6/C_8$ | 53 | 21 | 46 | 44 | 55 | 68 | 54 | 84 |
| Measured | | | | | | | | |
| (Predicted) | (17) | (13) | (1) | (18) | (1) | (25) | (1) | (12) |

These tests were carried out on a separate occasion, and using different apparatus, from those of Example 5, hence the slightly different scores.

The same trends as in Example 5 can be seen.

COMPARATIVE EXAMPLE

For the purposes of comparison, a pure $C_5/C_8$ sulphosuccinate was prepaed by the method of Example 2; the product of stage (i) of Example 2 was reacted, according to the procedure of stage (ii) of Example 2, with pentyl bromide (59 g, 0.39 mole) instead of hexyl bromide, and the product obtained was treated with sodium metabisulphite according to the procedure of stage (iii) of Example 2. The $diC_5$ sulphosuccinate was also prepared according to the procedure of Example 1, using 193.6 g (2.2 moles) of pentan-1-ol instead of the octanol/hexanol mixture.

The performance of the $C_5/C_8$ material was compared with the performances of the two corresponding symmetrical materials, and the results are shown in Table 4.

TABLE 4

| | 5° H. | | 24° H. | |
|---|---|---|---|---|
| Material | Normal soil | Casein soil | Normal soil | Casein soil |
| $diC_5$ | 0 | 0 | 0 | 0 |
| $diC_8$ | 40 | 28 | 1 | 37 |
| $C_5/C_8$ | 1 | 2 | 4 | 14 |
| Measured | | | | |
| (Predicted) | (20) | (14) | (~1) | (18) |

The performance of the known $C_5/C_8$ compound was found to be unacceptably low in each case, and except in the case of normal soil at 24°H, where the $diC_8$ compound itself performs unacceptably, it was considerably lower than the predicted performance.

EXAMPLE 7

This Example shows how the performance of the $diC_8$ compound is enhanced by the admixture of the $C_6/C_8$ compound of the invention. The results are shown in Table 5.

TABLE 5

| | 5° H. | | 24° H. | |
|---|---|---|---|---|
| Material (mole ratio where shown) | Normal soil | Casein soil | Normal soil | Casein soil |
| $diC_8$ | 40 | 28 | 1 | 37 |
| $C_6/C_8$ | 46 | 22 | 52 | 57 |
| $diC_8 + C_6/C_8$ 1:2 | 62 | 28 | 22 | 62 |

EXAMPLE 8

Example 7 was repeated using a range of ratios of the $diC_8$ material to the $C_6/C_8$ material. These tests were carried out on a different occasion, and using different apparatus, from those of Example 7, hence the slightly different scores for the individual materials. The results are shown in Table 6.

TABLE 6

| | 5° H. | | | | 24° H. | | | |
|---|---|---|---|---|---|---|---|---|
| Mole Ratio | Normal Soil | | Casein Soil | | Normal Soil | | Casein Soil | |
| $diC_8:C_6/C_8$ | Meas. | Pred. | Meas. | Pred. | Meas. | Pred. | Meas. | Pred. |
| $diC_8$ alone | 35 | — | 26 | — | 3 | — | 51 | — |
| 10:1 | 48 | (37) | 28 | (25) | 7 | (8) | 53 | (52) |
| 6:1 | 46 | (38) | 34 | (25) | 6 | (10) | 52 | (53) |
| 3:1 | 54 | (39) | 30 | (25) | 4 | (16) | 56 | (55) |
| 1:1 | 61 | (44) | 28 | (23) | 17 | (30) | 60 | (59) |
| 1:3 | 68 | (48) | 24 | (22) | 49 | (42) | 70 | (64) |
| 1:6 | 68 | (50) | 24 | (22) | 54 | (47) | 61 | (65) |
| 1:10 | 58 | (51) | 25 | (21) | 46 | (50) | 64 | (66) |
| $C_6/C_8$ alone | 53 | — | 21 | — | 55 | — | 68 | — |

Meas. = Measured
Pred. = Predicted

It will be noted that the scores are significantly higher than those obtained using the conventional dishwashing detergent system tested in Example 4. For good all-round performance the $C_6/C_8$ material of the invention preferably predominates.

EXAMPLE 9

The performance of the $C_6/C_8$ statistical mixture of Example 1 was then compared with that of the pure $C_6/C_8$ compound of Example 2. The results are shown in Table 7.

TABLE 7

| | 5° H. | | 24° H. | |
|---|---|---|---|---|
| Material | Normal soil | Casein soil | Normal soil | Casein soil |
| $C_6/C_8$ compound | 46 | 22 | 52 | 57 |
| $C_6/C_8$ statistical mixture | 53 | 28 | 42 | 66 |

It will be noted that the performance of the $C_6/C_8$ statistical mixture (25 mole percent $diC_6$, 25 mole percent $diC_8$, 50 mole percent $C_6/C_8$) is very close to, perhaps even slightly better than, that of the pure $C_6/C_8$ compound itself.

EXAMPLE 10

Example 9 was repeated using a wider range of water hardness. The results are shown in Table 8.

TABLE 8

| | 5° H. | | 16° H. | | 24° H. | | 36° H. | |
|---|---|---|---|---|---|---|---|---|
| | Normal soil | Protein soil | Normal soil | Protein soil | Normal soil | Protein soil | Normal soil | Protein soil |
| $C_6/C_8$ Compound | 53 | 21 | 46 | 44 | 55 | 68 | 54 | 84 |
| $C_6/C_8$ Statistical mixture | 61 | 31 | 42 | 52 | 49 | 65 | 24 | 54 |

Again it will be seen that the mixture gives in most cases very similar results to those of the compound itself.

EXAMPLE 11

In this experiment the foaming performance of a sulphosuccinate compound according to the invention in admixture with another detergent active material conventionally used in dishwashing (an alkyl ether sulphate) was investigated. The sulphosuccinates used in this test were the $C_6/C_8$ compound prepared in Example 2 and the statistical mixture prepared in Example 1, the alkyl ether sulphate was a Dobanol 25-3A as used in Example 4, and the weight ratio of sulphosuccinate to alkyl ether sulphate was 4:1. The performances of these systems were compared with those of corresponding mixtures of the symmetrical $diC_6$ and $diC_8$ sulphosuccinates with the alkyl ether sulphate at the same weight ratio of 4:1, the results being shown in Table 9; only normal soil was used in these tests.

TABLE 9

| Sulphosuccinate | 5° H. | 24° H. |
|---|---|---|
| $diC_8$ | 48 | 23 |
| $diC_6$ | 12 | 15 |
| $C_6/C_8$ compound | | |
| Measured | 48 | 87 |
| (Predicted) | (30) | (19) |
| $C_6/C_8$ mixture | | |
| Measured | 75 | 73 |

TABLE 9-continued

| Sulphosuccinate | 5° H. | 24° H. |
|---|---|---|
| (Predicted) | (39) | (53) |

EXAMPLE 12

In this experiment the effect of varying the ratio of sulphosuccinate to alkyl ether sulphate was investigated. The sulphosuccinate used was again the compound prepared in Example 2 and the alkyl ether sulphate was again Dobanol 25-3A. The results are shown in Table 10; only normal soil was used in this set of tests.

TABLE 10

| Material/ | 5° H. | | 24° H. | |
|---|---|---|---|---|
| weight ratio | Measured | (Predicted) | Measured | (Predicted) |
| Sulphosuccinate alone | 53 | — | 55 | — |
| 20:1 | 64 | (52) | 80 | (54) |
| 12:1 | 62 | (51) | 83 | (53) |
| 8:1 | 58 | (50) | 80 | (52) |
| 4:1 | 48 | (48) | 87 | (50) |
| 2:1 | 37 | (46) | 81 | (47) |
| 1:1 | 33 | (41) | 66 | (43) |
| 1:2 | 29 | (38) | 49 | (40) |
| 1:4 | 29 | (35) | 41 | (37) |
| Ether sulphate alone | 30 | — | 32 | — |

In 24°H hard water the measured score is higher than the predicted score at all ratios, and at ratios of 1:1 and above it is very substantially higher. In 5°H water, the measured score is higher than that predicted only at the higher ratios; ratios of 1:1 and above give better results than ether sulphate alone, ratios of 2:1 and above being preferred. For best all-round performance a ratio of 4:1 appears to be optimum.

EXAMPLE 13

Example 12 was repeated using the statistical mixture prepared in Example 1 instead of the $C_6/C_8$ compound prepared in Example 2. The results are shown in Table 11.

TABLE 11

| Material/ | 5° H. | | 24° H. | |
|---|---|---|---|---|
| weight ratio | Measured | (Predicted) | Measured | (Predicted) |
| Sulphosuccinate alone | 61 | — | 49 | — |
| 20:1 | 87 | (59) | 59 | (48) |
| 12:1 | 88 | (59) | 57 | (48) |
| 8:1 | 81 | (58) | 61 | (47) |
| 4:1 | 75 | (55) | 73 | (46) |
| 2:1 | 69 | (51) | 93 | (43) |
| 1:1 | 53 | (45) | 93 | (40) |
| 1:2 | 43 | (40) | 58 | (38) |

TABLE 11-continued

| Material/ | 5° H. | | 24° H. | |
|---|---|---|---|---|
| weight ratio | Measured | (Predicted) | Measured | (Predicted) |
| 1:4 | 36 | (36) | 44 | (35) |
| Ether sulphate alone | 30 | — | 32 | — |

EXAMPLE 14

In this experiment the dishwashing performance of a dialkyl sulphosuccinate/alkyl ether sulphate mixture was compared with that of an alkyl benzene sulphonate-/alkyl ether sulphate mixture using a plate washing test.

In the test, plates soiled with a starch/fat/fatty acid mixture were washed in a standard manner with 5 liters of test solution (total concentration 0.4 g/liter in 5°H or 24°H in water) in a bowl, until only a third of the surface of the solution in the bowl was covered with foam. The number of plates washed before this arbitrary endpoint was reached was taken as an indicator of dishwashing performance.

The composition according to the invention to be used in this test was a 4:1 by weight mixture of the statistical mixture prepared in Example 1 and the alkyl ether sulphate (Dobanol 25-3A) used in Example 4; and the comparison composition was a 4:1 by weight mixture of the alkyl benzene sulphonate (Dobs 102) used in Example 4 and the alkyl ether sulphate (Dobanol 25-3A) used in Example 4. The results, which clearly show the superiority of the sulphosuccinate-based composition, are shown in Table 12.

TABLE 12

| | Number of plates washed | |
|---|---|---|
| | 5° H. | 24° H. |
| Sulphosuccinate/alkyl-ether sulphate | 51 | 54 |
| Alkylbenzene sulphonate/alkyl ether sulphate | 33 | 28 |

EXAMPLE 15

In this experiment the dishwashing performance of a series of dilute solutions of the statistical mixture prepared in Example 1 was evaluated using a slightly different plate washing test method.

In the test, plates soiled with a wheat flour/soya oil/oleic acid/stearic acid soil were each prewetted with 10 ml of 4°H water and then washed, by the direct application thereto of a small quantity (2.5 ml) of the test product on a sponge prewetted with 26 ml of 4°H water. The number of plates washed, using a set procedure, before foam collapse occurred was taken as an indicator of dishwashing performance.

Dilute aqueous solutions of the sulphosuccinate mix at three different concentrations were prepared and tested, and for comparison three solutions of a linear $C_{10}$–$C_{13}$ alkylbenzene sulphonate (ex Deten, Brazil) were also prepared and tested. The results are shown in Table 13.

TABLE 13

| Concentration (weight %) | Number of plates washed | |
|---|---|---|
| | Sulphosuccinate Mix | Alkylbenzene Sulphonate |
| 11.5 | 20 | 12 |
| 5.0 | 14 | 8 |
| 2.5 | 10 | (not tested) |

From these results it can be inferred by interpolation that a solution of the sulphosuccinate mix having a concentration of about 3.5% would have a performance equivalent to that of the 11.5% alkylbenzene sulphonate solution.

EXAMPLE 16

In this Example the dishwashing performance of a sulphosuccinate/alkyl ether sulphate mixture was compared with that of an alkylbenzene sulphonate/alkyl ether sulphate mixture, using a third test method.

In this test, the plates used were soiled with a corn oil/oleic acid/stearic acid/rice starch soil, and each was prewetted with 7 ml of 5°H water. A sponge was dipped into 50 ml of a 4% solution (in 5°H water) of the test product and used to wash the plates using a set procedure, the number of plates washed before foam collapse occurred being taken as an indicator of dishwashing performance.

The products according to the invention used for this test were dilute aqueous solution of a 4:1 by weight mixture of the statistical mixture of Example 2 with the ether sulphate used in Example 4 (Dobanol 25-3A). The comparison products were dilute aqueous solutions of a 4:1 by weight mixture of a $C_{11}$–$C_{14}$ linear alkylbenzene sulphonate (ex Mitsubishi, Japan) and a $C_{11}$–$C_{13}$ oxo alcohol 3EO sulphate (Synperonic (Trade Mark) 3S-60 ex ICI). The test results are shown in Table 14.

TABLE 14

| Total Concentration (by weight %) | Number of plates washed | |
|---|---|---|
| | Sulphosuccinate Mix | Alkylbenzene Sulphonate |
| 15 | (not tested) | 17 |
| 7.5 | 24 | 10 |
| 3.75 | 14 | 7 |

Again, it can be inferred by interpolation that a sulphosuccinate/ether sulphate system having a total concentration of 5.5% by weight would have a performance equivalent to that of a 15% by weight alkylbenzene sulphonate/ether sulphate system.

EXAMPLE 17

The efficacy of a sulphosuccinate mix according to the invention as a shampoo detergent was investigated in the following experiment, in which the foaming capacity of the mix in the presence of simulated sebum was compared with those of some known shampoo detergents. The sulphosuccinate mix used was the $C_6/C_8$ statistical mixture prepared in Example 1, and the simulated sebum had the following composition:

| | Weight % |
|---|---|
| Triolein | 35.0 |
| Tristearin | 10.0 |
| Oleic acid | 10.0 |
| Stearic acid | 5.0 |
| Squalene | 35.0 |
| Cholesterol | 5.0 |

For each material tested, a 12% solution in 14°H water was prepared (this simulates a typical shampoo composition in the bottle) and was then diluted by a factor of 9 (this simulates the dilution of a shampoo by the consumer immediately before and during application to the hair). 1 g of artificial sebum was added to a fixed volume (180 ml) of each diluted (1.33%) solution, mechanical agitation was effected using a food mixer rotating at 600 rpm, and the volume of foam generated after 2 minutes was measured. The results are shown in Table 15.

TABLE 15

| Detergent-active Material | Foam Volume (ml) |
| --- | --- |
| Dodecyl benzene sulphate | 40 |
| Monoalkyl sulphosuccinate (Condanol (Trade Mark) SBFA/3) | 110 |
| Sodium lauryl ether (2EO) sulphate | 130 |
| Monoethanolamine lauryl sulphate | 200 |
| Sulphosuccinate mix | 240 |

It will be seen that in this in vitro test the sulphosuccinate mix of the invention produces significantly higher volumes of foam than do the conventional shampoo detergents sodium lauryl ether sulphates and monoethanolamine lauryl sulphate. The monoalkyl sulphosuccinate performs substantially worse than the dialkyl sulphosuccinate mix of the invention.

EXAMPLE 18

Using the procedure of Example 17, the effect of diluting the initial solution from 12% to 6% was investigated. The results are shown in Table 16.

TABLE 16

| Detergent-active Material | Concentration of initial solution (weight %) | Foam Volume (ml) |
| --- | --- | --- |
| $C_6/C_8$ sulphosuccinate mix | 12% | 250 |
|  | 6% | 225 |
| Sodium lauryl ether sulphate | 12% | 120 |

The results show that even using half the concentration of detergent-active material in the initial solution, a result significantly better than that for the conventional material at the higher concentration is obtained.

EXAMPLE 19

In this experiment the removal of clay soil from fabrics by a material according to the invention was compared with that by a conventional fabric washing detergent-active agent, in a tergotometer test. The material according to the invention was the statistical mixture prepared in Example 1, and the comparison material was a linear $C_{10}$–$C_{15}$ alkyl benzene sulphonate (Dobs (Trade Mark) 055 ex Shell).

In each case a wash liquor (500 ml) was prepared containing, in demineralised water, 0.1 g/liter or 0.2 g/liter of the detergent-active material and 1 g/liter of sodium metaborate tetrahydrate buffer. 10 g of illite-clay-soiled polyester cotton test cloth pieces were added and the liquor was agitated at 90 cycles/minute for 30 minutes at 25° C. The amount of clay soil removed from the test cloth was calculated from the reflectance increase, as measured by means of a Carl Zeiss Elrepho reflectometer.

The results were as follows:

| Detergent-active material | Soil removed (%) | |
| --- | --- | --- |
|  | 0.1 g/l | 0.2 g/l |
| Sulphosuccinate | 61 | 68 |
| Alkylbenzene sulphonate | 53 | 63 |

We claim:

1. A compound of the formula I

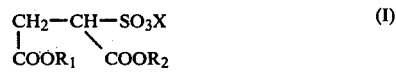

wherein one of $R_1$ and $R_2$ represents a $C_6$ alkyl group and the other represents a $C_8$ alkyl group, and X represents a monovalent cation or 1/m of an m-valent cation.

2. The compound of claim 1, wherein at least one of $R_1$ and $R_2$ is a straight-chain alkyl group.

3. The compound of claim 1, wherein X is selected from the group consisting of alkali metal, ammonium, substituted ammonium and magnesium ions.

4. In a detergent composition comprising one or more detergent-active materials in admixture or conjunction with one or more detergent adjuncts, the improvement which comprises including as detergent-active material a compound of the formula I

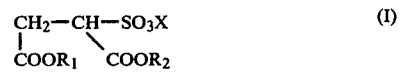

wherein one of $R_1$ and $R_2$ represents a $C_6$ alkyl group and the other represents a $C_8$ alkyl group, and X represents a monovalent solubilising cation or 1/m of a solubilising m-valent cation.

5. The detergent composition of claim 4, which is a liquid.

* * * * *